United States Patent [19]

Redmore

[11] 4,442,286

[45] Apr. 10, 1984

[54] PREPARATION OF AMINES BY THE REDUCTION OF IMINES WITH PHOSPHOROUS ACID

[75] Inventor: Derek Redmore, Ballwin, Mo.

[73] Assignee: Petrolite Corporation, St. Louis, Mo.

[21] Appl. No.: 732,604

[22] Filed: Oct. 15, 1976

[51] Int. Cl.³ .................... C07D 295/02; C07C 85/08; C07C 85/00
[52] U.S. Cl. ..................................... 544/178; 546/184; 546/348; 564/385; 564/391; 564/446; 564/448; 564/472; 564/473; 564/484
[58] Field of Search .............. 260/247, 296 R, 293.65, 260/563, 570.9; 544/178; 546/184, 348; 564/385, 391, 446, 448, 472, 473, 484

[56] References Cited

U.S. PATENT DOCUMENTS 3,288,846 11/1966 Irani et al. ........................ 260/502.5

OTHER PUBLICATIONS

Wagner et al., Syn. Org. Chem.", (1953), p. 662.
"The Condensed Chemical Dictionary", van Norstrand Reinhold, eighth ed., (1971), p. 688.

Primary Examiner—Robert W. Ramsuer
Attorney, Agent, or Firm—Sidney B. Ring; Leon J. Bercovitz

[57] ABSTRACT

This invention relates to the preparation of amines by the reduction of imines with phosphorous acid, preferably under basic conditions.

13 Claims, No Drawings

PREPARATION OF AMINES BY THE REDUCTION OF IMINES WITH PHOSPHOROUS ACID

Patent application Ser. No. 713,705 filed Aug. 12, 1976 now U.S. Pat. No. 4,235,809 describes and claims a process for the reaction of phosphorous acid with imines to yield α-amino phosphonic acids by an addition process. This is illustrated by the following equation:

Equation I

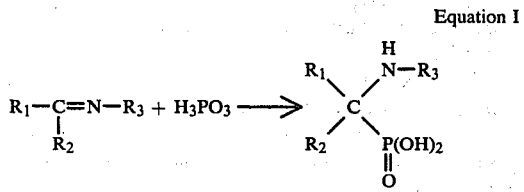

I have now discovered that certain imines of the formula in Equation I favor the addition reaction as described in Equation I whereas other imines favor the reduction reaction as illustrated in Equation II.

Equation II

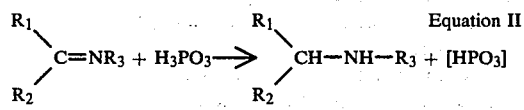

I have discovered that where $R_1$ and/or $R_2$ is an aryl group, the addition reaction of Equation I will predominate but where $R_1$ and $R_2$ are alkyl or hydrogen, or joined as a cycloalkyl group, the reduction process of Equation II will predominate.

The reduction reaction is also applicable to enamines, for example according to the following Equation III.

Equation III

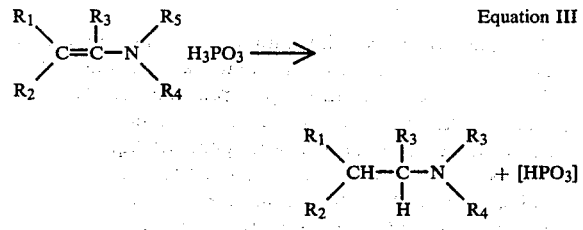

Examples of enamines include those derived from acyclic aldehydes and ketones such as those formed from secondary amines and aldehydes and ketones as well as enamines of cyclic ketones

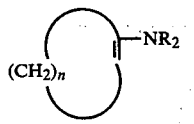

morpholino-cyclopentene, morpholino-cyclohexene, pyrrolidinocyclohexene, etc.

In addition, I have further discovered that where the reaction is carried out under basic conditions such as in the presence of an amine, for example such as trialkyl amine, reduction becomes substantially the exclusive reaction.

I have further discovered that as an extension of the reduction process involving the in situ formation of imine, amines can be methylated with formaldehyde and phosphorous acid, for example in accord with the following reaction Equation IV

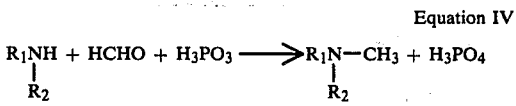

where $R_1$ is alkyl, aralkyl, cycloalkyl, etc. and $R_2$ is H, alkyl, etc., and $R_3$ is alkyl, aryl, cycloalkyl, alkaryl, aralkyl and heterocyclic.

The reaction is carried out by reacting an imine with $H_3PO_3$ in substantially stoichiometric amounts. An excess of $H_3PO_3$ may be employed if desired.

In general, the reaction is carried out at any suitable temperature such as from about 60° to 180° C., for example from about 70° to 160°, but preferably from about 80° to 140° C.

The reduction reaction is promoted by the presence of a base, for example tertiary amines such as a trialkylamines, for example, triethylamine, tripropylamine, etc. Other amines that can be employed are as follows: Dimethylcyclohexylamine, dimethylhexylamine, N-methyl pyrrolidine, N-methyl piperidine, etc.

The concentration of amine present in reaction should be sufficient to render the reaction mixture basic such as in a concentration of from about 0.05 to 5 moles, for example from about 0.1 to 3 moles, such as from about 0.2 to 2 moles, but preferably from about 0.3 moles to 1.5 moles.

The imines are derived from any amine capable of reacting with an aldehyde or ketone to form an imine. Examples of amines which can be employed to form imines are of the general formula

R $NH_2$ where R is alkyl, aralkyl, cycloalkyl, alkenyl, heterocyclic, etc.

ALKYL

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, eicosyl, docosyl, etc. having 1-50 or more carbons, such as 1-30, but preferably 12-18 carbons.

The term "alkyl" also includes isomers of the straight chain group wherein branching occurs along the chain, for example

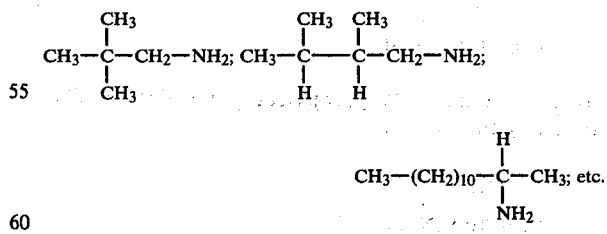

ALKENYL

These include unsaturated analogous (for example, 2-50, such as 2-30 carbon atoms) of alkyl groups containing one or more —C=C— groups, for example, decenyl, dodecenyl, tridecenyl, tetradecenyl, pentadecenyl, hexadecenyl, heptadecenyl, octadecentyl, etc., dienes for example octadienyl, etc., trienes, for example octatrienyl, etc.

CYCLOALKYL

These include:

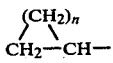

for example cyclobutyl, cyclopentyl, cyclohexyl, cycloheptyl, cyclooctyl, etc.; substituted derivatives thereof, for example alkyl or polyalkyl, for example alkyl cyclohexyl, dialkyl cyclohexyl, etc.

The following are examples of commercial amines. The nomenclature of such amines is derived from either their chain length or source of raw materials, for example, Armeen 8D-Octyl amine
Armeen C-Coconut oil amine
Armeen S-Soybean oil amine
Armeen T-Tallow amine
Armeen O-Oleyl amine
Armeen HT-Hydrogenated tallow amine
Products with "D" designate distilled grade. Products without "D" designate technical grade.

Polyamines containing more than one primary amine can be employed such as contain 2 or more primary amines. Examples of diamines are of the general formula

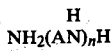

where A is alkylene, for example having 1-10 or more carbons, and n is 1 to 10 or more, for example
$NH_2CH_2CH_2CH_2NH_2$
$NH_2CH_2CH_2CH_2CH_2NH_2$
1-6-hexamethylenediamine
1-10-decamethylenediamine
Other suitable amines are exemplified by:
$CH_2-OCH_2CH_2CH_2NH_2$
$CH_2-OCH_2CH_2CH_2NH_2$
1-2-diaminocyclohexane
Di-(2-aminoethyl) ether
Di-(2-aminoethyl) sulfide
Polyalkylene polyamines, etc.

Polyalkylene polyamines are illustrated by Polyethylene polyamines of the formula

n=1-10 or more. Polypropylene polyamines as illustrated by the formula

polyhexylene polyamines as illustrated by the formula

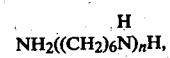

etc. n=1-10.

The aldehyde or ketone employed in forming the imine by reacting with amines is of the general formula

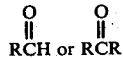

where R is alkyl, aryl, alkaryl, aralkyl, cycloalkyl, heterocyclic, etc. The R group may also be joined together to form a cyclic group such as cycloalkanones, etc.

Specific examples are as follows: Acetaldehyde, propionaldehyde, butyraldehyde, isobutyraldehyde, valeraldehyde, 2-ethylbutyraldehyde, hexaldehyde, 2-ethylhexaldehyde, etc. Benzaldehyde, tolualdehyde, furfuraldehyde, pyridine carboxaldehyde. Acetone, methylethylketone, etc. Cycloalkanones, cyclopentanone, cyclohexanone, cycloheptanone, alkylated derivatives, acetophenone, etc.

Many of the above aldehydes and ketones can react with secondary amines to yield enamines. See A. G. Cook, "Enamines," Marcel Dekker, 1969. Useful secondary amines include dimethylamine, diethylamine, dipropylamine, dibutylamine, etc. Unsymmetrical amines such as methylbenzylamine, methylcyclohexylamine, etc. Cyclic amines such as morpholine, piperidine, pyrrolidine, etc.

The following examples are presented for purposes of illustration and not of limitation.

EXAMPLE 1

Preparation of N-benzylcyclohexylamine

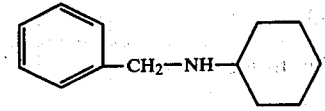

The imine from cyclohexanone and benzylamine was prepared in benzene in the normal way. To this imine (37.4 g; 0.2 mole) was added phosphorous acid (16.4 g; 0.2 mole) and the mixture stirred while heating. The reaction mixture became a homogeneous liquid at 70° and at 95°-100° a vigorous reaction took place. After keeping at 110°-130° for 30 minutes the mixture was cooled and diluted with water. Basification with NaOH and extraction with benzene gave after evaporation of the solvent N-benzylcyclohexylamine (80%). Distillation gave pure N-benzylcyclohexylamine bp 120°-125°/3 mm.

EXAMPLE 2

N-Benzyl (4-pyridyl) methylamine.

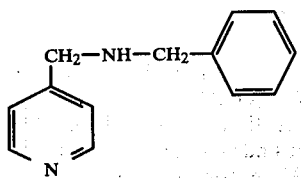

To the imine from pyridine-4-carboxaldehyde and benzylamine (20 g; 0.1 mole) was added phosphorous acid (8.4 g; 0.1 mole) and the mixture heated at 110°-130° for 1½ hours. After cooling to 90° water (150 ml) was added. The aqueous solution was basified with NaOH and extracted with benzene (3×100 ml). Evaporation of the solvent gave the N-benzyl(4-pyridyl) methylamine 14.9 g (74%). Nmr measurements, $^1$H and $^{13}$C, confirmed the structural assignment.

EXAMPLE 3

N-Benzylisobutylamine

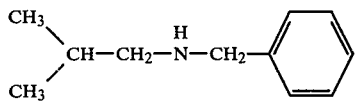

To the imine from isobutyraldehyde and benzylamine (48.4 g; 0.3 mole) was added phosphorous acid (24.6 g; 0.3 mole) and the mixture slowly warmed while stirring. As the internal temperature reached 70°–75° a vigorous exothermic reaction ensued taking the temperature to 130°–135°. After maintaining at 130°–140° for 30 mins. the viscous product was cooled to 100° and diluted with water. Basification and extraction with chloroform gave crude amine after solvent evaporation. Distillation gave pure N-benzylisobutylamine, 13.6 g (28%) bp 94°–99°/5.6 mm. Nmr confirmed the assigned structure.

EXAMPLE 4

Illustration of the effect of added basic tertiary amine in the reduction process.

(a) Without added amine to yield predominately phosphonic acid derivative.

The imine from benzaldehyde and benzylamine (65 g; 0.33 mole) was added to phosphorous acid (27.3 g; 0.33 mole) and the mixture stirred with heating. As the temperature reached 95°–100° the whole mixture became a homogeneous liquid which reacted vigorously as the temperature reached 115°–120°. The reaction mass became very viscous and was allowed to cool to a glass. This glass was dissolved in aqueous sodium carbonate and upon acidification gave N-benzyl α-aminobenzylphosphonic acid, mp 233°–4°, 90 g (98%).

Analysis: Calculated for $C_{14}H_{16}NO_3P$; N, 5.05; P, 11.18. Found: N, 4.91; P, 11.05.

(b) With added tertiary amine to yield predominately the amine by reduction of the imine.

The imine from benzaldehyde and benzylamine (19.5 g; 0.1 mole) was heated with phosphorous acid (8.2 g; 0.1 mole) and triethylamine (10.1 g; 0.1 mole) for 2 hours at reflux (125°–130°). After cooling to 90° the reaction mixture was diluted with water (50 ml), basified (NaOH) and extracted with chloroform. The extract was concentrated by evaporation of the chloroform and triethylamine to yield dibenzylamine 19.3 g (98% yield).

I have also discovered that the presence of certain organic solvents such as alcohols, etc. favors the reduction reaction rather than the addition reaction. Examples of suitable solvents include the following: alkanols such as methyl alcohol, propyl alcohol, butyl alcohol, pentyl alcohol, hexyl alcohol, heptyl alcohol, octyl alcohol, decyl alcohol and higher aliphatic alcohols, aralkyl alcohols such as benzyl alcohol, substituted benzyl alcohols, etc.

This effect of such solvents is illustrated in the following examples.

EXAMPLE 5

The effect of added alcohol

N-Benzylidenemethylamine (Ph—CH=NCH$_3$) when heated with phosphorous acid alone gives exclusively the addition product N-methyl α-aminobenzylphosphonic acid.

N-Benzylidenemethylamine (11.9 g; 0.1 mole), phosphorous acid (8.2 g; 0.1 mole) and n-butanol (22 g) were heated at gentle reflux (115°–118°) for 3 hours. After cooling water was added and the aqueous mixture basified. Extraction with chloroform and distillation of the residue gave N-methylbenzylamine 4.7 g (39%). Nmr spectra confirmed the structural assignment.

The following examples illustrate reduction of enamines.

EXAMPLE 6

Preparation of N-cyclopentyl morpholine by the reduction of an enamine

1-Morpholinocyclopentene (30 g; 0.2 mole) was mixed with phosphorous acid (16.4 g; 0.2 mole) and heated with stirring. As the temperature reached 70° an exothermic process took place taking the internal temperature to 105°. The viscosity of the reaction mixture increased as the reaction proceeded. After maintaining at 100°–105° for 30 mins. the reaction mixture was diluted and basified. Extraction with chloroform yielded N-cyclopentylmorpholine (72%). The product was characterized by $^{13}$C and $^1$H nmr spectra.

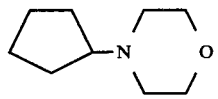

EXAMPLE 7

Reduction of an enamine 1-morpholinocyclohexene (32.3 g; 0.19 mole) and phosphorous acid (15.9 g; 0.19 mole) were heated together with stirring to 100° and maintained for 1 hour. Dilution with water, basification with NaOH and extraction with chloroform gave 29.7 g (91% of N-cyclohexylmorpholine after evaporation of the solvent.

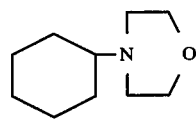

EXAMPLE 8

Reduction of an enamine

The piperidine enamine of isobutyraldehyde (31.9 g; 0.23 mole) was mixed with phosphorous acid (18.8 g; 0.23 mole) and heated to 100° with stirring. As this temperature was reached an exothermic reaction took place resulting in a viscosity increase in the reaction mixture. After allowing to cool to 85° water was added and the mixture basified. Extraction with benzene gave 16.3 g (50%) of N-isobutylpiperidine. The product was characterized by Nmr spectra.

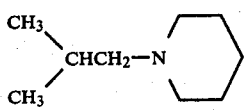

The following examples illustrate reductive methylation reactions.

EXAMPLE 9

To benzylamine (16.9 g; 0.16 moles) was added a solution of phosphorous acid (13.0 g; 0.16 mole) in 40% aqueous formaldehyde (13 g) during 30 mins. with slight cooling. The mixture was carefully warmed whereupon an exothermic reaction took place. After cooling the reaction mixture was diluted with water and basified to recover the amine products which were isolated by extraction with chloroform. The reaction product was shown to consist of a mixture of unreacted benzylamine (38%), N-methylbenzylamine (24%) and N,N-dimethylbenzylamine (38%) by a combination of Glc and proton nmr.

EXAMPLE 10

A solution of phosphorous acid (32.8 g; 0.4 mole) in 40% aqueous formaldehyde (40 ml; 0.5 mole) was added dropwise with stirring during 30 mins. to benzylamine (21.4 g; 0.2 mole). No cooling was applied during the addition which was exothermic. The reaction mixture was heated at reflux for 2 hours upon completion of the addition. After cooling the reaction mixture was basified and extracted with benzene. Evaporation of the solvent followed by distillation yielded pure N,N-dimethylbenzylamine 19.5 g (72%) bp 179°–180°.

EXAMPLE 11

To a solution of cyclohexylamine (26.3 g; 0.27 mole) in water (50 ml) was added a solution of phosphorous acid (44 g; 0.54 mole) in aqueous formaldehyde (49 g; 0.6 mole) during 90 mins. After the addition the reaction mixture was heated at reflux for 2 hrs. and allowed to cool. Basification and extraction with chloroform yielded crude amine. Distillation gave pure N,N-dimethylcyclohexylamine, 18.2 g (54%), bp 150°–154°.

EXAMPLE 12

A solution of phosphorous acid (24.6 g; 0.3 mole) in 40% aqueous formaldehyde (32 ml; 0.4 mole) was added at 10°–15° (ice bath cooling) to morpholine (26.1 g; 0.3 mole) in water (20 ml) during 30 mins. The solution was then heated at reflux for 4 hrs., cooled, basified and extracted with benzene. After removal of benzene careful distillation gave N-methylmorpholine, 16.3 g (54%), bp 114°–6°.

EXAMPLE 13

Reduction of cyclic amine product—the reaction product of an aldehyde and ethylenediamine, for example of the formula:

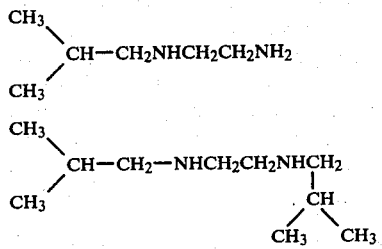

The imidazolidine from isobutyraldehyde and ethylenediamine (22.8 g; 0.2 mole) was heated with phosphorous acid (16.4 g; 0.2 mole) at 100°–120° for 3 hours. After cooling water and base were added. Extraction with chloroform and evaporation gave crude amine. Distillation gave 12 g of a mixture of mono and diisobutylethylenediamine, bp 160°–170°.

$$CH_3\!\!\diagdown\!\!\!\!\!\!\!\diagup CH-CH_2NHCH_2CH_2NH_2$$
$$CH_3$$

$$CH_3\!\!\diagdown\!\!\!\!\!\!\!\diagup CH-CH_2-NHCH_2CH_2NHCH_2$$
$$CH_3 \qquad\qquad\qquad\qquad CH$$
$$\qquad\qquad\qquad\qquad CH_3\ \ CH_3$$

Glc and nmr indicated the product contained approximately equal amounts of mono and dialkylated ethylenediamine.

I claim:

1. A process of preparing amines which comprises reducing imines of the formula

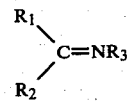

where $R_1$ and $R_2$ are hydrogen, alkyl or $R_1$ and $R_2$ may be joined to form a cycloalkyl group, and $R_3$ may be alkyl, aryl, cycloalkyl, alkaryl, aralkyl or heterocyclic, or enamines with phosphorous acid.

2. The process of claim 1 where an aldehyde and phosphorous acid are first mixed and the mixture then added to an amine whereby an imine or enamine is formed in situ and the final product is an amine.

3. The process of claim 1 where the reaction is carried out at temperatures between about 60° C. to about 180° C.

4. The process of claim 1 where the imine or enamine and the phosphorous acid are reacted in substantially stoichiometric amounts.

5. The process of claim 1 where an excess of phosphorous acid is employed.

6. A process of preparing amines which comprises reducing imines or enamines with phosphorous acid under basic conditions or in the presence of an alcohol solvent.

7. The process of claim 6 where the reaction is carried out under basic conditions.

8. The process of claim 7 where the basic condition is effected with an organic amine.

9. The process of claim 8 where the organic amine is triethylamine.

10. The process of claim 6 where the reaction is carried out in the presence of an alcohol solvent.

11. The process of claim 10 where the alcohol solvent is n-butanol.

12. The process of claim 2 where the in situ reaction involves the reaction of an amine, formaldehyde and phosphorous acid.

13. The process of claim 12 wherein there is reacted benzylamine, formaldehyde and phosphorous acid.

* * * * *